(12) United States Patent
Solomon

(10) Patent No.: US 9,770,425 B2
(45) Date of Patent: Sep. 26, 2017

(54) IMPLANTABLE BONE MARROW ACCESS APPARATUS

(71) Applicant: APERTURE MEDICAL TECHNOLOGY LLC, New York, NY (US)

(72) Inventor: Stephen Solomon, New York, NY (US)

(73) Assignee: APERTURE MEDICAL TECHNOLOGY LLC, New York, NY (US)

( * ) Notice: Subject to any disclaimer, the term of this patent is extended or adjusted under 35 U.S.C. 154(b) by 0 days.

(21) Appl. No.: 15/024,522

(22) PCT Filed: Jun. 18, 2015

(86) PCT No.: PCT/US2015/036407
§ 371 (c)(1),
(2) Date: Mar. 24, 2016

(87) PCT Pub. No.: WO2016/057090
PCT Pub. Date: Apr. 14, 2016

(65) Prior Publication Data
US 2017/0035396 A1 Feb. 9, 2017

Related U.S. Application Data

(60) Provisional application No. 62/062,105, filed on Oct. 9, 2014.

(51) Int. Cl.
*A61B 10/02* (2006.01)
*A61M 39/02* (2006.01)
(Continued)

(52) U.S. Cl.
CPC .......... *A61K 31/198* (2013.01); *A61B 10/025* (2013.01); *A61K 33/04* (2013.01);
(Continued)

(58) Field of Classification Search
CPC . A61B 10/02–10/06; A61B 2010/0258; A61B 17/3472–17/3476;
(Continued)

(56) References Cited

U.S. PATENT DOCUMENTS

| 4,142,517 A | 3/1979 | Contreras Guerrero de Stavropoulos et al. |
| 4,403,617 A | 9/1983 | Tretinyak |

(Continued)

FOREIGN PATENT DOCUMENTS

| GB | 1324759 A | 7/1973 |
| GB | 2289415 A | 11/1995 |
| WO | 2014070804 A1 | 5/2014 |

OTHER PUBLICATIONS

International Search Report and Written Opinion for PCT/US2015/036407 dated Sep. 30, 2015.

*Primary Examiner* — Devin Henson
*Assistant Examiner* — Matthew Kremer
(74) *Attorney, Agent, or Firm* — Holtz, Holtz & Volek PC

(57) ABSTRACT

Bone marrow access apparatus includes a bone attachment part attachable to bone, a tubular conduit part attached to the bone attachment part and defining a conduit communicating with a hollow interior of the bone attachment part, and a port attached to the conduit part. The port defines a hollow interior communicating with the conduit defined by the conduit part. One or more optional flow control components are arranged in a passage defined by the interior of the bone attachment member, the conduit of the conduit part and the interior of the port and operatively restrict inflow or outflow. A localization part is on or integrated into the port and enables the port to be located through skin. In use, a sampling device is inserted through skin overlying the port, into and through the passage defined by the apparatus, (Continued)

through the flow control component(s), when present, and into the marrow space. Marrow is captured and then the sampling device is removed.

13 Claims, 7 Drawing Sheets

(51) Int. Cl.
  *A61M 39/06* (2006.01)
  *A61K 31/198* (2006.01)
  *A61K 33/04* (2006.01)
  *A61K 45/06* (2006.01)

(52) U.S. Cl.
  CPC ......... *A61K 45/06* (2013.01); *A61M 39/0208* (2013.01); *A61M 39/06* (2013.01); *A61B 2010/0258* (2013.01); *A61M 2039/0202* (2013.01); *A61M 2039/025* (2013.01); *A61M 2039/0282* (2013.01); *A61M 2202/10* (2013.01)

(58) Field of Classification Search
  CPC .......................... A61M 39/02–39/0693; A61M 2039/0202–2039/0686; A61M 2202/10; A61K 31/198; A61K 33/04; A61K 45/06
  See application file for complete search history.

(56) References Cited

U.S. PATENT DOCUMENTS

| | | | |
|---|---|---|---|
| 4,738,261 A | 4/1988 | Enstrom | |
| 4,772,261 A | 9/1988 | Von Hoff et al. | |
| 5,332,398 A | 7/1994 | Miller et al. | |
| 5,451,210 A | 9/1995 | Kramer et al. | |
| 5,456,267 A | 10/1995 | Stark | |
| 5,727,770 A * | 3/1998 | Dennis | A61B 17/3462 251/149.1 |
| 6,018,094 A | 1/2000 | Fox | |
| 6,165,168 A * | 12/2000 | Russo | A61M 39/045 604/247 |
| 7,670,328 B2 | 3/2010 | Miller | |
| 7,833,204 B2 | 11/2010 | Picha | |
| 7,951,089 B2 | 5/2011 | Miller | |
| 8,142,365 B2 | 3/2012 | Miller | |
| 8,372,061 B2 | 2/2013 | Berna et al. | |
| 8,419,683 B2 | 4/2013 | Miller | |
| 8,690,791 B2 | 4/2014 | Miller | |
| 8,715,287 B2 | 5/2014 | Miller | |
| 8,801,670 B2 | 8/2014 | Drontle et al. | |
| 8,870,872 B2 | 10/2014 | Miller | |
| 8,876,826 B2 | 11/2014 | Miller | |
| 8,992,535 B2 | 3/2015 | Miller | |
| 8,998,848 B2 | 4/2015 | Miller et al. | |
| 9,072,543 B2 | 7/2015 | Miller et al. | |
| 9,078,637 B2 | 7/2015 | Miller | |
| 2003/0032922 A1* | 2/2003 | Moorehead | A61M 25/0631 604/110 |
| 2003/0225344 A1 | 12/2003 | Miller | |
| 2004/0127905 A1 | 7/2004 | Lim | |
| 2005/0148940 A1 | 7/2005 | Miller | |
| 2006/0167378 A1 | 7/2006 | Miller | |
| 2006/0167379 A1 | 7/2006 | Miller | |
| 2006/0167416 A1* | 7/2006 | Mathis | A61B 10/0275 604/164.01 |
| 2007/0197935 A1 | 8/2007 | Reiley et al. | |
| 2007/0270712 A1 | 11/2007 | Wiksell et al. | |
| 2007/0270775 A1 | 11/2007 | Miller et al. | |
| 2008/0015467 A1 | 1/2008 | Miller | |
| 2008/0015468 A1 | 1/2008 | Miller | |
| 2008/0215056 A1 | 9/2008 | Miller et al. | |
| 2008/0287910 A1* | 11/2008 | Picha | A61B 17/3472 604/507 |
| 2009/0054808 A1 | 2/2009 | Miller | |
| 2010/0137740 A1 | 6/2010 | Miller | |
| 2010/0234761 A1 | 9/2010 | Cortes Ramirez et al. | |
| 2010/0298784 A1 | 11/2010 | Miller | |
| 2011/0076640 A1 | 3/2011 | Jones | |
| 2011/0218644 A1* | 9/2011 | Meridew | A61F 2/3662 623/23.15 |
| 2012/0095440 A1 | 4/2012 | Islam | |
| 2012/0116247 A1* | 5/2012 | Wawrzyniak | A61B 10/025 600/567 |
| 2014/0018699 A1* | 1/2014 | Rusnak | A61B 10/0233 600/566 |
| 2014/0150782 A1* | 6/2014 | Vazales | A61M 16/0463 128/202.16 |
| 2014/0288499 A1 | 9/2014 | Miller | |
| 2015/0314118 A1* | 11/2015 | Kelekis | A61M 39/02 604/502 |

\* cited by examiner

IMPLANTABLE BONE MARROW ACCESS APPARATUS

FIELD OF THE INVENTION

The present invention relates generally to a bone marrow access apparatus capable of providing easy, repeatable access to a patient's bone marrow, and a bone marrow aspiration and/or biopsy method using the bone marrow access apparatus.

BACKGROUND OF THE INVENTION

Bone marrow is the major site of blood cell formation and, while at birth it is found within nearly all bones, by adolescence it is located primarily within axial bones (e.g., pelvis and femur). The bone marrow exists in the inner portion of bones, referred to herein as the marrow space, and contains the precursor stem cells that ultimately become red blood cells, white blood cells, and platelets.

Bone marrow aspirations and biopsies are common tests used to evaluate the bone marrow for leukemias and other hematologic disorders, for example. A sampling of the marrow from the marrow space can determine cell number, cell shape, and cell maturation. Special pathologic stains and molecular studies on the marrow specimens can establish certain diagnoses. Sampling of marrow from the marrow space may occur at multiple times during a patient's treatment program to assess progress.

Current techniques for sampling bone marrow generally require needle penetration of bone each time a sample is taken, which can be painful for the patient. In patients who require multiple samplings during their care, this can be a repeated painful episode. It may require additional trips to the hospital and repeated anesthesia events.

An apparatus that is often used for sampling bone marrow is shown in FIGS. 13 and 14. The apparatus 150 includes a bone penetration needle 152 that has an operative portion 154 extending through a cannula 156 as shown in FIG. 13 to contact and penetrate the bone (not shown in FIG. 13). After such penetration, the bone penetration needle 152 is removed from engagement with the cannula 156 which remains in place, as shown in FIG. 14. An aspiration or biopsy needle 158 is passed through the cannula 156 into a marrow space of a bone 160 to retrieve marrow, and then withdrawn from the cannula 156. Other sampling devices or exchange apparatus such as a wire are also commonly used through the cannula.

Another technique for sampling bone marrow is described in U.S. Pat. No. 8,690,791 and utilizes bone harvesting apparatus that includes a driver operable to be releasably engaged with an intraosseous device. The intraosseous device includes a cannula having a first end that penetrates bone and bone marrow and to allow retrieval of portions of bone and/or bone marrow. The cannula has a second end releasably engaged with bone marrow sampling equipment. A removable trocar has an inner channel that conveys portions of bone and/or bone marrow and a side port communicating with the inner channel.

Another procedure that requires needle penetration of bone is intraosseous infusion. In intraosseous infusion, a resuscitative fluid or drug solution is injected directly into the bone marrow of the patient's bone through an intramedullary infusion device, from where it is transported throughout the patient's body.

One intramedullary access device for use in intraosseous infusions is described in U.S. Pat. No. 7,833,204 and includes a tubular conduit having a closed distal end and a proximal end with a length sufficient to pass through the cortical region and extend into the cancellous region of a bone. A flange circles the outside of the proximal end of the conduit. A penetrable diaphragm is positioned within the tubular conduit that extends into the bone. Outlet structures are positioned along the outer side surfaces of the tubular conduit, each creating an outlet opening so as to allow fluid flow between the tubular conduit and the cancellous region of the bone. A compressible member is positioned over the outlet openings at the distal end of the tubular conduit.

OBJECTS AND SUMMARY OF THE INVENTION

An object of one or more embodiments of the present invention is to provide a bone marrow access apparatus and method that allow repeated sampling of bone marrow at multiple timepoints without the need for repeated bone punctures through the bone cortex (the outer portion of the bone that has nerves which make punctures painful). The subcutaneous location of the device may reduce infection from repeated sampling.

A bone marrow access apparatus in accordance with the invention includes a bone attachment part or member adapted to be attached to bone and having a hollow interior, a tubular conduit part or member attached to the bone attachment member and defining a conduit communicating with the interior of the bone attachment member, and a port attached to the conduit member. The port includes a housing defining a hollow interior communicating with the conduit defined by the tubular member. The interior of the bone attachment member, the conduit of the tubular member and the hollow interior of the housing of the port define a passage in which a flow control component is arranged. A localization part or member is on or integrated into the port and configured to enable the port to be located through skin that covers the port and allows alignment of the needle with the channel through the device from the exterior.

The bone attachment member, tubular conduit member and localization member may be parts in the sense that they are all formed on a common, unitary structure along with the port. This one-piece structure provides the functionality of the various members. Alternatively, different combinations of the parts may be formed on the same component.

The localization member may be a palpable structure on an upper surface of the housing of the port, e.g., one or more bumps discernible when running fingers along skin over the port. The port also may include an attachment structure to enable the port to be attached to the conduit.

The conduit member may be flexible. The flow control component may be a valve, a diaphragm or other type of restrictor, and possibly arranged in the bone attachment member, in the conduit of the tubular member or in the housing of the port. The conduit member may be permanently fixed to the bone attachment member and the port, or attached to the port only after the conduit member is shortened during installation of the bone marrow apparatus.

A bone marrow apparatus installation method in accordance with the invention includes making an incision in a patient and then attaching a bone attachment member to the bone in a position in which a hollow interior of the bone attachment member is in flow communication with a marrow space in the bone. One end region of a tubular conduit member is attached to a housing of the bone attachment member. The tubular member defines a conduit in flow communication with the hollow interior of the bone attachment member. A port is attached to an opposite end region of the conduit member, and includes a housing defining a hollow interior communicating with the conduit defined by the conduit. The port also includes a localization member configured to enable the port to be located through skin that covers the port. Once the bone attachment member is attached to the bone, the incision is closed with the localization member in a position under skin of the patient.

To accommodate different size patients and different placements of the apparatus, the method may entail shortening the conduit to a length dependent on the distance between the bone attachment member and the port when in an installed state. The conduit is thus provided with a larger or maximum length and then shortened to size during installation. In thin patients, for example, there may be only a port that communicates with the bone attachment member and no conduit. Similarly, the port member may be shortened/heightened dependent on the patient.

The bone attachment member may be attached to the bone by screwing the bone attachment member into the bone using screw threads on an outer surface of the bone attachment member. Other fixing techniques are also possible.

The end of the conduit may be attached to the housing of the bone attachment member by fixing the end of the conduit to the housing of the bone attachment member prior to attaching the bone attachment member to the bone, i.e., the bone attachment member and the conduit are a unit ready for installation.

Another embodiment of a bone marrow access apparatus in accordance with the invention includes an access port including an interior passage and attachment means to attach the access port to a bone. The access port is configured to be attached to the bone to cause the interior passage to define part of a conduit leading to a marrow space in the bone. A flow control component is in the interior passage, and a localization member is on or integrated into the access port and configured to enable the access port to be located through skin covers the access port. A bone marrow sampling instrument is operatively insertable through the flow control component, and through the interior passage into the marrow space when the interior passage defines part of the passage leading to the marrow space in the bone.

The access port may include a housing defining an internal channel extending through an interior of the housing, in which case, the attachment means may be arranged on the housing, and the flow control component may be arranged in the housing. A covering is connected to the housing and defines an internal channel aligning with the internal channel of the housing. The internal channel of the covering and the housing define the interior passage of the access port. The internal channel of the covering may have a funnel shape to guide the sampling device into the passage.

A method for performing a bone marrow biopsy in accordance with the invention includes, in an installation stage, attaching a bone attachment member to a bone in a position in which a hollow interior of the bone attachment member is in flow communication with a marrow space in the bone. One end region of a tubular conduit member is attached to a housing of the bone attachment member. The tubular member defines a conduit in flow communication with the hollow interior of the bone attachment member that communicates with the bone marrow. A port is attached to an opposite end region of the tubular member. The port includes a hollow interior communicating with the conduit defined by the tubular member. Then, the port is covered with skin of the patient with the localization member in a position under the skin of the patient.

The port is initially localized under the skin. In each of at least one bone marrow biopsy stage, a sampling device is inserted through the skin above the port, through the hollow interior of the port, into the conduit defined by the tubular member, through the flow control component and through the hollow interior of the bone attachment member into the marrow space. Marrow is captured from the marrow space using the sampling device, and then the sampling device is removed from the marrow space through the port, the tubular member and the bone attachment member. Repeat sampling is possible by repeating the steps through the guide needle.

Additionally, in the biopsy stage before inserting the sampling device, it is possible to insert a trocar or guide needle through the skin above the port, and through the hollow interior of the port until the trocar engages with the port and then rotating the trocar relative to the port to fix the trocar to the port. The trocar defines a guide for insertion of the sampling device into the passage to the marrow.

When the port includes a palpable structure as the localization member, in the biopsy stage before inserting the sampling device, the port can be located by feeling along the skin for the palpable structure on the port. Different techniques would be used for other localization members, for example magnetic localization. Localization of the port enables alignment of the needle exterior to the patient with the conduit within the device.

The device may or may not be removed from the patient when the clinical need for bone marrow access is no longer present.

BRIEF DESCRIPTION OF THE DRAWINGS

The present invention will be more fully understood from the following detailed description of embodiments thereof, taken together with the drawings, in which.

DETAILED DESCRIPTION OF THE INVENTION

Figure 1:
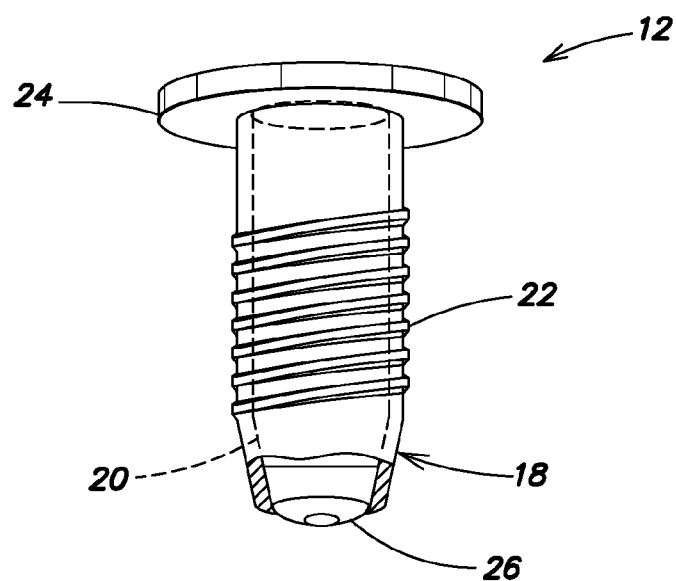
FIG. 1 shows a bone attachment member used in a bone marrow access apparatus in accordance with the invention, partly in section.
Figure 2:
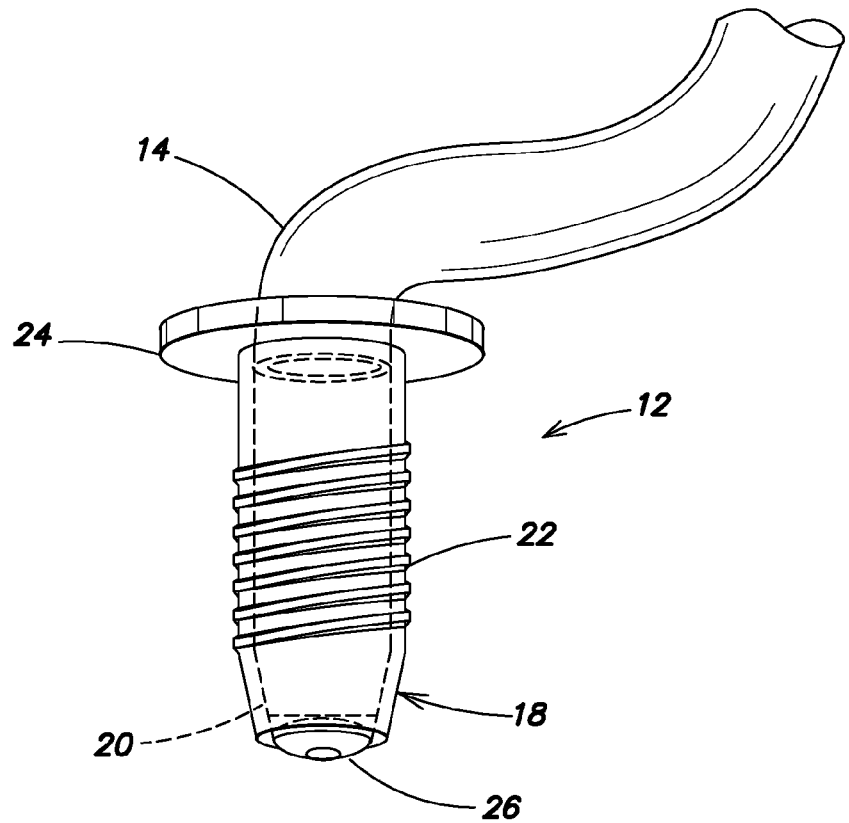
FIG. 2 shows the bone attachment member of FIG. 1 and a flexible, tubular conduit member attached thereto.
Figure 3:
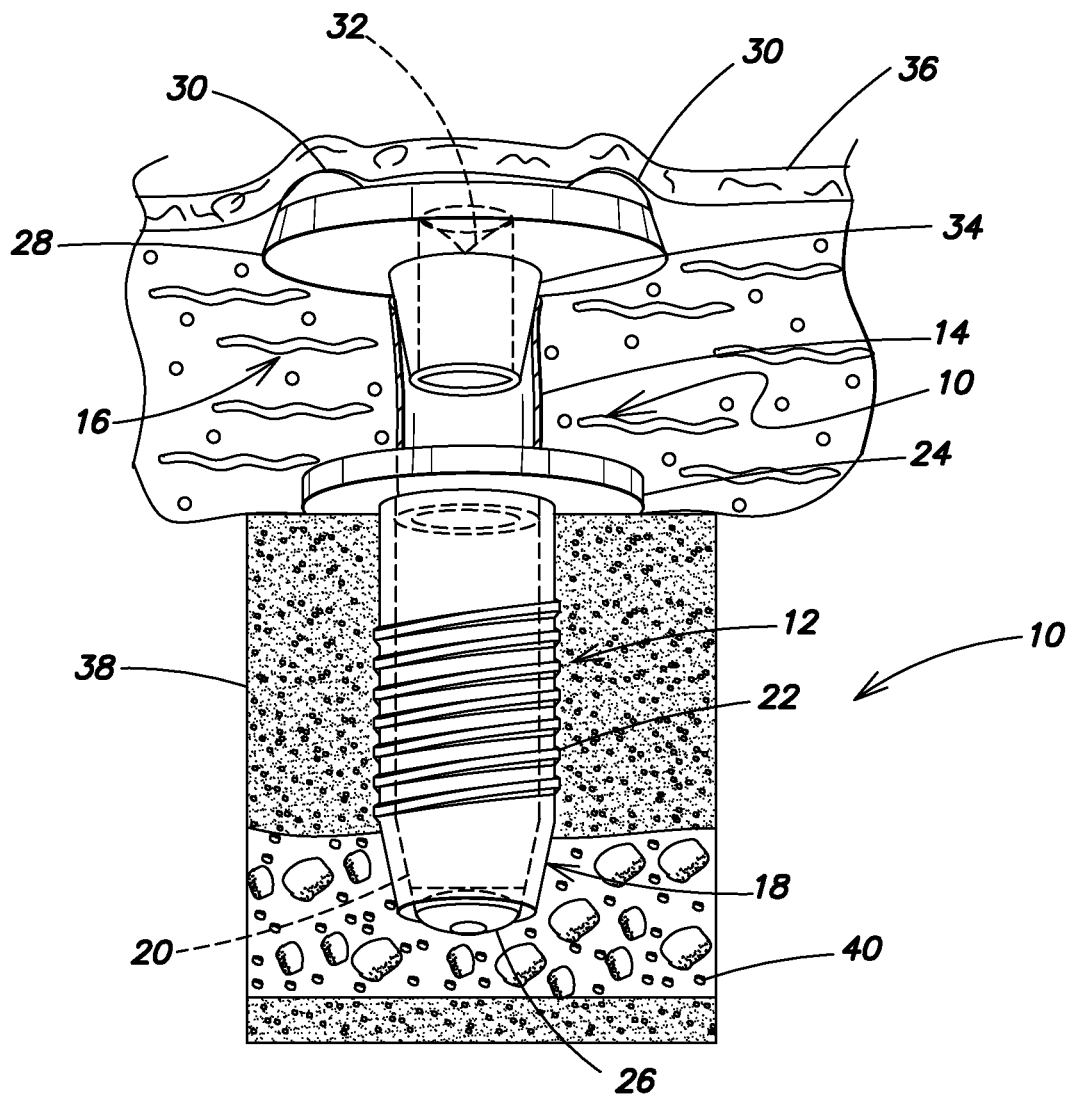
FIG. 3 shows a completed bone marrow access apparatus in accordance with the invention, including the bone attachment member shown in FIGS. 1 and 2 and the tubular conduit member shown in FIG. 2.

Referring to the accompanying drawings wherein like reference numbers refer to the same or similar elements, FIGS. 1-3 show a first embodiment of a bone marrow access apparatus 10 in accordance with the invention. Bone marrow access apparatus 10 includes three main components, namely a bone attachment member 12 that is attached to the cortex of the bone, a tubular conduit member 14 that is attached at one end to the bone attachment member 12 and a port 16 that is attached to the opposite end of the conduit member 14.

The bone attachment member 12 is shown in FIG. 1 and comprises a cylindrical housing 18 defining a hollow interior 20, and that has optional screw threads 22 on an outer surface. As such, the bone attachment member 12 may also be referred to herein as a hollow screw. The housing 18 is provided with known means to enable its placement through the cortex of the bone using a screwdriver or similar known tool. The housing 18 also includes a flange 24 that is designed to rest on the bone cortex when the bone attachment member 12 is properly attached to the bone, i.e., such that the distal end of the housing 18 is present in the marrow space in the bone.

Bone attachment member 12 also includes a valve 26 at the distal end of the housing 18 that will be present in the marrow space when the bone attachment member 12 is properly attached to the bone. Valve 26 enables regulation of the removal of bone marrow from the marrow space. The particular type of valve 26 may vary depending on the environment of use or other commercial considerations, but in one embodiment, the valve 26 is a ball valve.

The valve 26 represents a restrictor in that it restricts entry of material into the hollow interior of the bone attachment member 12, such as entry of a sampling device into the hollow interior the bone attachment member 12 that would be operatively used during extraction of bone marrow, and/or restricts flow of material into or through the hollow interior of the bone attachment member 12. Alternative restrictors may also be used in the invention, such as, but not limited to, a diaphragm. Such restrictors may also be considered flow control components because they control the flow of material, e.g., regulate, allow or prevent an object to pass into the interior of the component associated with the flow control component.

FIG. 2 shows the conduit member 14 attached to the bone attachment member 12. Conduit member 14 may be flexible and reinforced to enable it to be maintained below the skin of a patient and avoid perforation. To this end, the conduit member 14 is made of a biocompatible material known to those skilled in the art to which this invention pertains.

The conduit member 14 may be permanently fixed to an inside surface of the housing 18 as shown in FIG. 2. In one embodiment, the conduit member 14 has a length larger than the largest expected operative length and then is cut down to the specific needed size for the patient after attachment of the bone attachment member 12 to the patient's bone. This length is roughly the length between the site at which the bone attachment member 12 is attached to the bone and the site of the port 16.

Alternatively, different bone marrow access apparatus 10 may be formed, each with a different length conduit member 14. The surgeon then selects the appropriate sized apparatus 10 depending on the patient's physical dimensions.

FIG. 3 shows the attachment of the port 16 to the conduit member 14. Part 16 includes a housing 28, palpable structure 30 on the upper surface of the housing 28, e.g., bumps or other structure known to those skilled in the art of subcutaneous medical ports, a valve 32 on the housing that enables controlled insertion of a tool through a hollow interior of the housing 28, and an attachment structure 34 to enable the port 16 to be attached to the end of the conduit member 14 in a position in which the hollow interior of the housing 28 aligns with the interior passage 14A defined by the conduit member 14.

The palpable structure 30 is discernible by feeling the patient's skin 36, and thus serves to enable easy location of the port 16. More generally, the palpable structure 30 represents a localization member that is provided on the port 16, whether on the housing 28 or elsewhere, that is configured to enable the port 16 to be located through an opaque covering that covers the port 16, i.e., the skin of the patient in which the bone marrow access apparatus 10 is implanted. Similar structure that accomplishes the same function, i.e., to enable the port 16 to be located under the skin by, for example, tough or sight, may also be used in the invention and is considered part thereof. For example, it is possible to incorporate a light into the port 16 and activate the light to enable the port 16 to be visible when present below the patient's skin. The light would therefore be considered the localization member. It is also possible to magnetize the port 16 or a part thereof, i.e., provide a part of metallic material, and use a magnet to find the port 16 when covered by the patient's skin. In this case, the magnet would be considered the localization member.

In another embodiment, the localization member is the port 16 itself. In this embodiment, the port 16 is configured to enable it to be located under skin, e.g., by providing it with a specific shape (e.g., round) and structure (e.g., rigid) so that one can feel along the patients skin for the port 16 and use the shape of the port 16 to enable alignment of a needle with the passage.

When performing a sampling operation to access bone marrow using the bone marrow access apparatus 10, the individual performing the sampling would interact with localization member to find the port 16. This interaction depends on the type of the localization member and would be, for example, feeling along the skin of the patient if the localization member were palpable structure 30, or looking for the light if the localization member were a light incorporated into the port 16, or pass a magnet along the skin if the localization member were a magnetized part of the port 16. The interaction can thus take a variety of different forms. In addition to localization, the localizing features allow centering of the sampling device to align with the internal passage through the device.

The localization member facilitates alignment of the external sampling needle or biopsy instrument with the passage defined by the interior of the bone attachment member 12, the conduit of the tubular conduit member 14 and the hollow interior of the housing of the port 16. This alignment allows for easy sampling and retrieval of bone marrow from the bone to which the bone attachment member 12 is attached.

As shown in FIG. 3, the port 16 is directly above the bone attachment member 12, providing a minimum length of the conduit member 14 for the specific patient. However, the port 16 is not required to be directly above the bone attachment member 12.

To install the apparatus 10 into a patient, the site on the bone 38 to position the bone attachment member 12 will be determined, in a manner known to those skilled in the art to which this invention pertains, and the bone attachment member 12 is then screwed into the bone 38 using an appropriate tool (not shown). The screw threads 22 facilitate this insertion, as well as retention of the bone attachment member 12 in the bone 38. The size of the bone attachment member 12 is dimensioned to at least reach to the marrow space. The variability in depth of the bone attachment member is another approach to managing varying patient sizes. Thus, there may be a plurality of different sizes of bone attachment members 12, and a suitable size is selected based on the bone 38 to which it is being attached and the size of the patient.

Once the bone attachment member 12 is fully inserted, the conduit member 14 is attached to the housing 18 (if it is not pre-attached to the housing 18, which is equally viable possibility). The conduit member 14 is then shortened or cut to fit the patient, i.e., provide the appropriate length between the bone attachment member 12 and the expected site of the port 16 below the patient's skin 36. This distance may be the same as the distance between the bone attachment member 12 and the patient's skin 12. The port may be superficial and palpable while the bone is deeper to the skin.

The port 16 is then attached to the free end of the conduit member 14 via the attachment structure 34. This attachment may be force-fit or any other attachment technique used to attach a sheath-like conduit member to a housing. The port itself may have varying heights to account for patient size. If a fixed size conduit member 14 is used, the port 16 may be pre-attached to the conduit member 14.

Installation of the apparatus 10 is now complete. The incision site is then covered by the patient's skin 36, with the localization member in a position below and preferably adjacent the skin to enable its easy location when needed for a sampling procedure.

In use to remove bone marrow from the bone marrow space 40, the surgeon would feel along the patient's skin 36 for the palpable structure 30 in order to locate the port 16. Once located, the surgeon would insert a biopsy needle or guide needle penetrating the skin 36 above the valve 32, into the valve 32, through the hollow interior of housing 28, into the passage 14A defined by the conduit member 14 and then through the hollow interior of the bone attachment member 12 into the marrow space. Marrow is captured and then the biopsy needle is removed.

Figure 4:
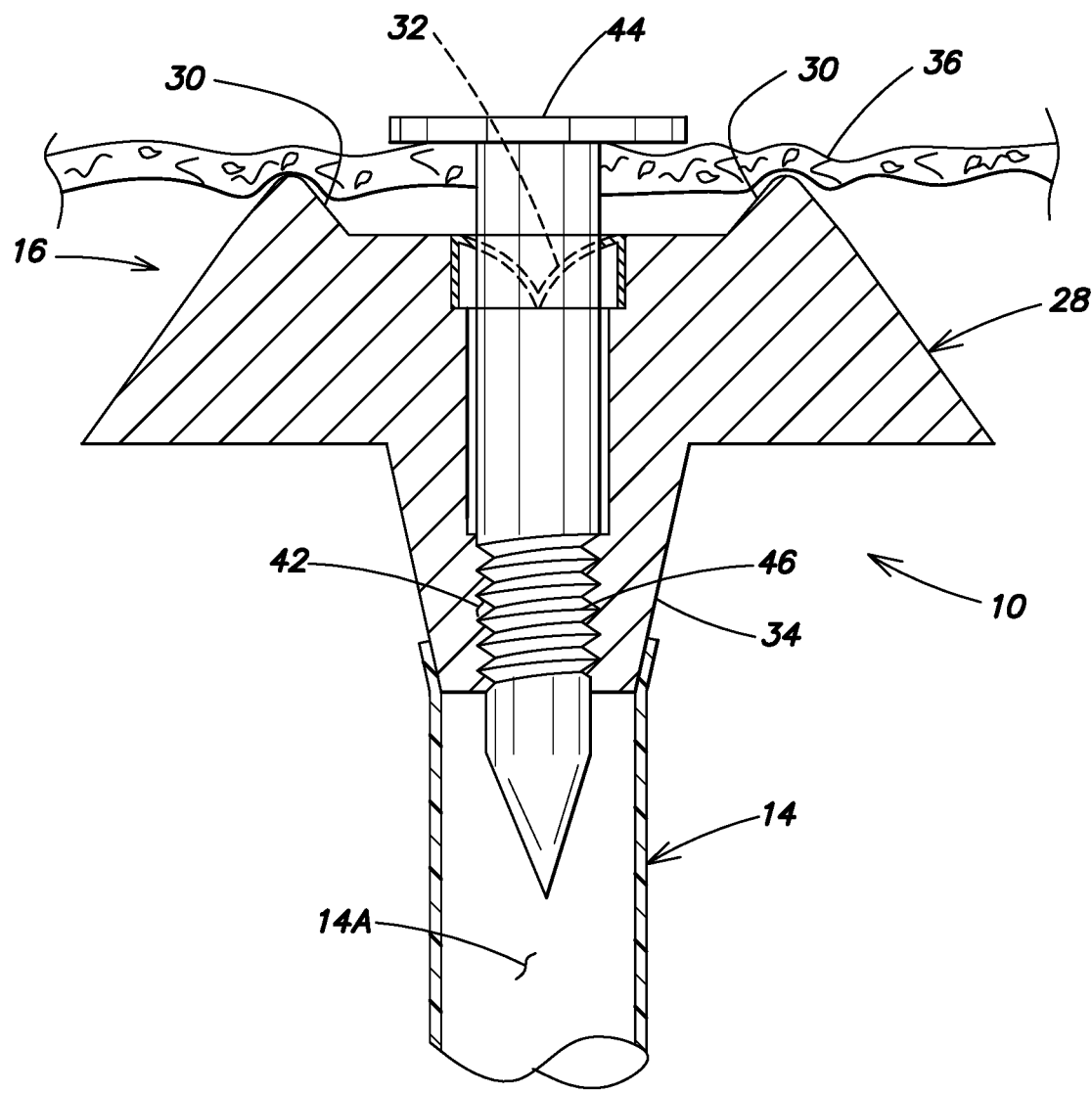
FIG. 4 shows use of a trocar to aid insertion of a biopsy needle into the tubular conduit member.
Figure 5:
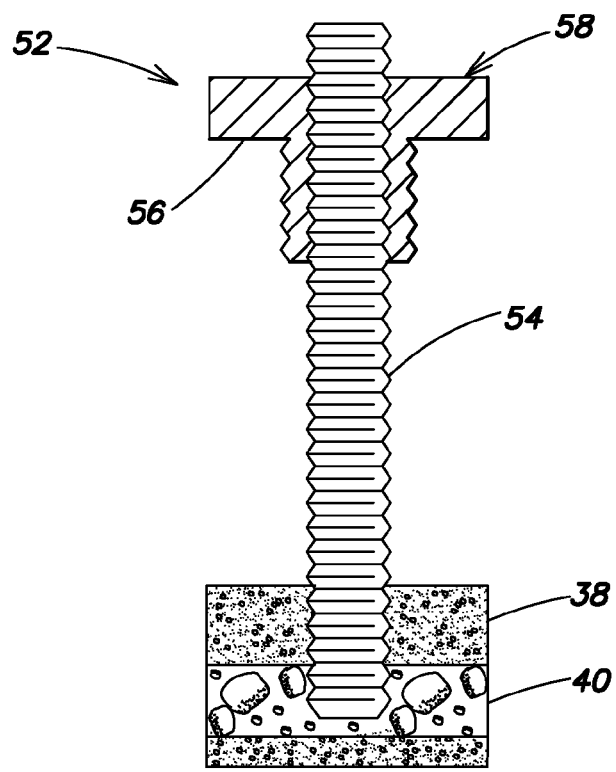
FIG. 5 shows the manner in which an access port of a third embodiment of bone marrow access apparatus in accordance with the invention is installed in connection with bone.

To aid in the insertion of the biopsy needle into the passage 14A defined by the conduit member 14, an interior surface of the housing 28 may be provided with threads 42, and a trocar 44 provided with complementary threads 46, see FIG. 4. The trocar 44 is initially inserted through the patient's skin 36 and into the valve 32 until its threads 46 engage threads 42. The trocar 44 is then rotated to attach it to the port 16. Thereafter, the biopsy needle is inserted through the trocar 44 directly into the passage 14A defined by the conduit member 14.

Additional modifications of the bone marrow apparatus 10 are contemplated as being within the scope of the invention, and include other features disclosed herein to the extent not incompatible with the above structure.

For example, it is possible to construct the bone marrow access apparatus as a single piece including the bone attachment member 12, the tubular conduit member 14 and the port 16. The single piece bone marrow access apparatus would be configured to provide the functionality of these three elements. A unitary bone marrow access apparatus would thereby be formed. It is also possible to combine two of the three elements into a single piece, e.g., the bone attachment member 12 and the tubular conduit member 14, which would provide the functionality of the two combined elements.

In another embodiment, it is possible to dispense with the tubular conduit member 14 and connected the bone attachment member 12 directly to the port 16. The bone attachment member 12 and/or port 16 may be constructed to enable the port 16 to be close to the skin of the patient when the bone marrow access apparatus is installed. This embodiment may be useful when there is a very small distance between the bone and the skin of the patient.

Figure 6:
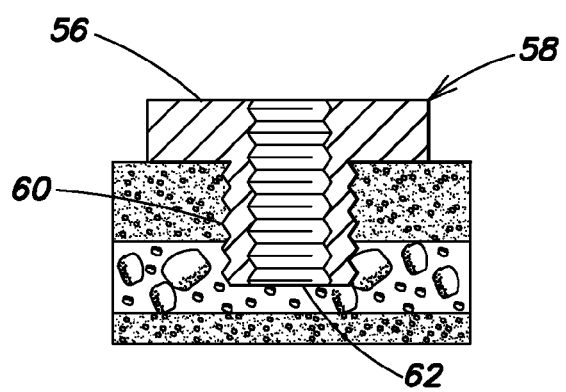
FIG. 6 shows the completed installation of the access port shown in FIG. 5.
Figure 7:
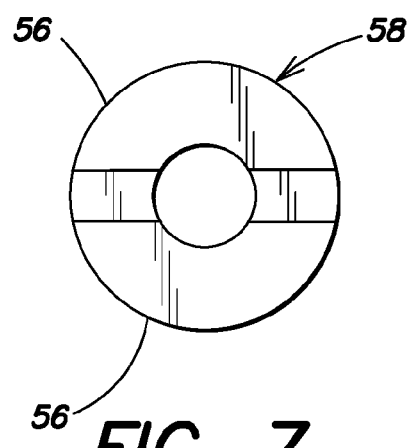
FIG. 7 is a top view of the installed access port shown in FIG. 6.

FIGS. 5-10 relate to an embodiment of a bone marrow access apparatus 50 that does not include a tubular conduit member or sheath. Bone marrow access apparatus 50 includes an access port 52 that is supra-osseous, i.e., formed on the bone 38. To install such an access port 52, the access port 52 may be threaded down a rod 54 that extends into the marrow space 40 of the bone 38 (FIG. 5) until it reaches a position in which flanges 56 of a housing 58 of the access port 52 rest against the bone 38 (FIG. 6). This threading may be achieved using a screwdriver when the upper surface of the access port 52 including a portion of the flanges 56 is provided with screwdriver fittings (see FIG. 7). The flanges 56 thus define, in part, a tool engagement surface to enable installation of the housing 58 on the bone 38 by the tool.

When the access port 52 is designed for use with a screwdriver, the screwdriver can help thread the access port 52 into the bone 38 so that at least a portion of the housing 58 is in an opening previously formed at the bone penetration site. The housing 58 thus includes one or more threads 60 that are threaded into opening of the bone 38 upon rotation of the housing 58 by the screwdriver (or other installation tool). To this end, a lower, projecting portion 62 of the housing 58 penetrates through the outer surface of the bone 38 when the housing 58 rests on the bone 38 (see FIG. 8). The thread or threads 60 is/are formed on this projecting portion 62. Other means for attaching the housing 58 to the bone 38 known to those skilled in the art to which this invention pertains, in addition to the use of one or more threads 60 on the housing 58, are also within the scope of the invention, all of which are considered attachment means herein. The rod 54 is removed after the access port 52 is threaded into the bone 38.

Figure 8:
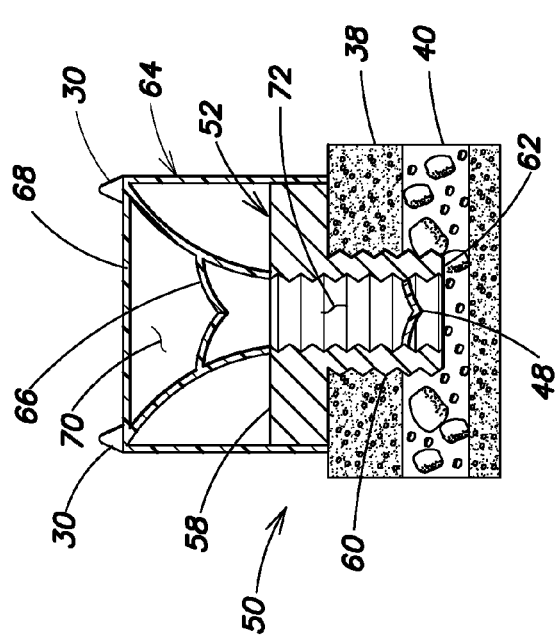
FIG. 8 shows a covering on the installed access port shown in FIG. 6.

A penetrable covering 64 is then placed over the access port 52, and includes one or more restrictors, for example, a valve 66, and an elastomer diaphragm, valve, or seal 68 positioned above the valve 66, and a channel 70 between the elastomer diaphragm 68 and the valve 66 (FIG. 8). The elastomer diaphragm 68 and valve 66 allow repeated penetration by needle or forceps for aspiration or biopsy. Although both are shown in FIG. 8, only one may be included. Although the diaphragm 68 and other diaphragms mentioned herein are preferably made of an elastomer, other materials may be used, which materials would be apparent to those skilled in the art and are considered to be within the scope of the invention.

A channel 72 is situated below the valve 66 and extends through the access port 52. If access port 52 is used as a replacement for port 16 (in the embodiment of FIGS. 1-3 described above) or with an internal conduit 104 (in the embodiment of FIGS. 11 and 12 described below), then the channel 72 would communicate with the passage 14A defined by the conduit member 14 or the passage defined by the internal conduit 104.

The diameter of the housing 58 may be about twice the diameter of the internal channel 72.

The channel 70 and/or channel 72 may each be funneled to direct the external needle, forceps or sampling device to the orifice 62 of the access port 52, or entrance of the passage 14A defined by the conduit member 14 or entrance of the passage defined by the internal conduit.

A valve 48 may be arranged at the distal end of the channel 72 of the housing 58. This valve 48 is useful to prevent inflow of material from the marrow space 40 into the channel 72, thereby keeping the channel 72 relatively clean and free from unwanted material between marrow extractions. Although shown with one valve 66 in the internal channel 70 of the covering 64 and another valve 48 in the internal channel 72 of the housing 58, both valves may be arranged in the covering 64 or both valves may be arranged in the housing 58. Generally then, an interior passage of the access port 52, i.e., the combination of internal channels 70, 72, includes two valves 48, 66.

Additional coverings 64 may be stacked to bring access to the device more superficial and closer to the skin. Each covering 64 can be attached to the one below it (not shown) in a manner known to those skilled in the art.

Figure 9:
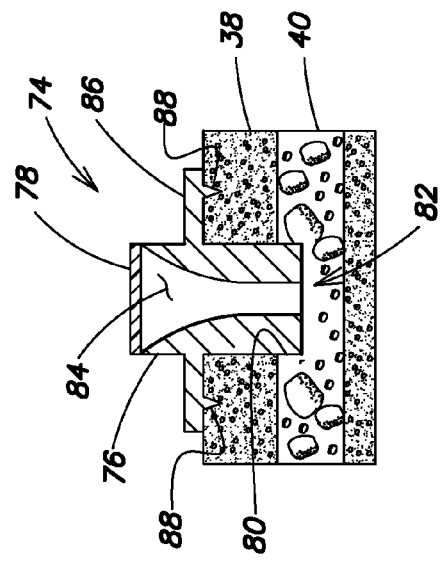
FIG. 9 shows another embodiment of an access port of a bone marrow access apparatus in accordance with the invention.

FIG. 9 shows another embodiment of an access port 74 for a bone marrow access apparatus in accordance with any of the embodiments disclosed herein, but which does not include a tubular conduit member. Access port 74 has a housing 76 and an elastomeric diaphragm or covering 78 attached to the housing 76 and formed as a covering button over an opening 80 at the bone penetration site 82. A conduit member or sheath is not required in this embodiment and thus, the internal channel 84 of the housing 76 leads directly to the marrow space 40. Flanges 86 are provided on the housing 76. A distance between the flanges 86 is longer than a diameter of the penetration site 82. The flanges 86 may each include one or more bone securement or securing members 88 such as tacks or nails that are configured to function as bone securement members to secure the housing 76 with respect to the bone 38.

Figure 10:
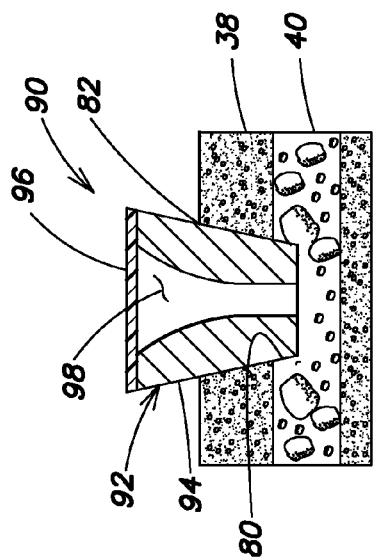
FIG. 10 shows yet another embodiment of an access port of a bone marrow access apparatus in accordance with the invention.

FIG. 10 shows yet another embodiment of an access port 90 for a bone marrow access apparatus in accordance with any of the embodiments disclosed herein, also with use of a conduit member 14. Access port 90 is wedged or corked and does not include flanges. The access port 90 includes a housing 92 having an inwardly tapering outer surface 94 defined by one or more walls. The inward taper allows the access port 90 to be wedged into the opening 80 at the bone penetration site 82. An elastomer diaphragm or covering 96 is attached to the upper end of the housing 92. Lacking the conduit member 14, the internal channel 98 of the housing 92 leads directly to the marrow space 40 as in the embodiment described with reference to FIG. 9.

Figure 11:
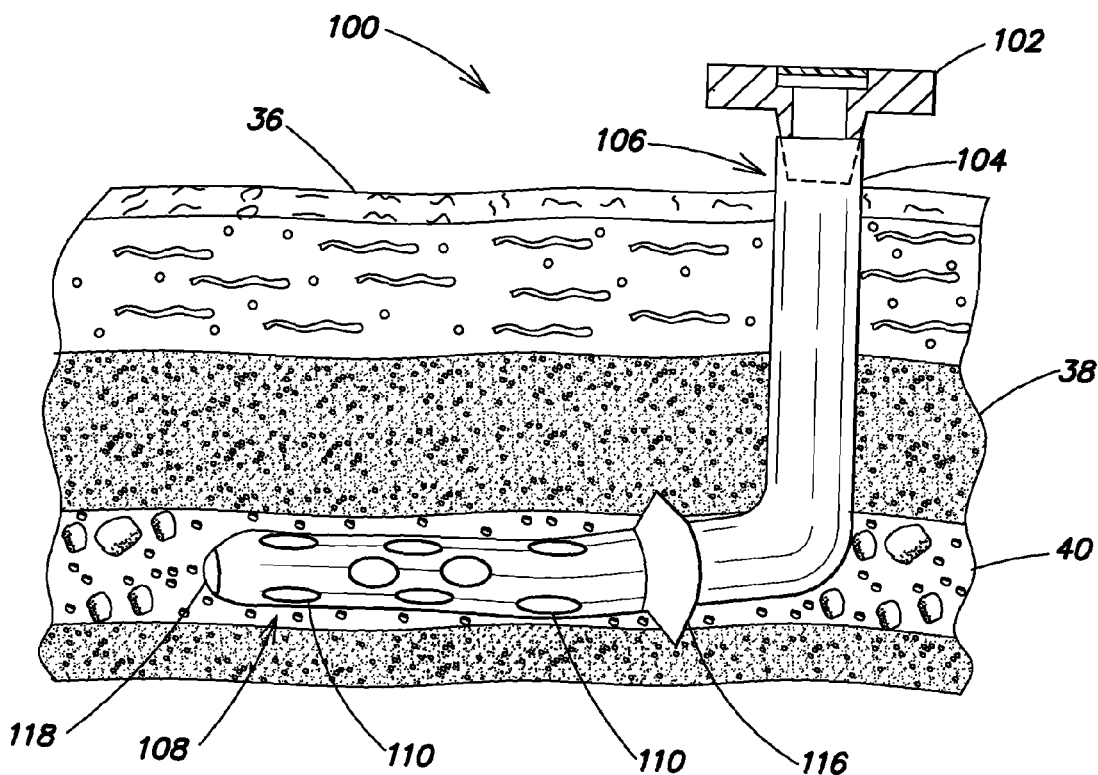
FIG. 11 shows another embodiment of bone marrow access apparatus in accordance with the invention.

FIG. 11 shows an embodiment of a bone marrow access apparatus 100 in accordance with the invention with an access port 102 at a proximal end external to the patient and a conduit 104 having a proximal end 106 connected to the access port 102 and a distal end 108. The distal end 108 of the conduit 104 includes multiple side holes 110 adapted to be positioned within the marrow space 40 of the patient's bone 38. Conduit 104 is designed to penetrate the bone 38 with a portion or all of the distal end 108 inside of the bone 38 and a remaining portion, if any, outside of the bone 38.

The conduit 104 also includes an internal retention (Malecot retention) device 116 that retains the conduit 104 in place in connection with the bone 38. The retention device 116 may be situated proximally to the side holes 110, but on that portion of the distal end 108 that will be secured in the marrow space 40 of the bone 38. Other retaining structure that fixes a tube in connection with the body known to those skilled in the art may be used to retain the conduit 104 in connection with the bone 38. For example, the conduit 104 may be configured as a catheter and may have a Malecot winged formation within the marrow space 40 or a pigtail to help secure it within the intramedullary space or retention barbs to avoid inadvertent dislodgment.

The distal end 108 of the conduit 104 lying within the bone 38 may be a catheter with multiple holes for aspiration, e.g., like side holes 110. The conduit 104 may also include an end hole 118 for biopsy forceps penetration.

The access port 102 includes a housing with an internal channel that communicates with the conduit 104. Access port 102 also includes an elastomer diaphragm, valve and/or covering over the internal channel (described in other embodiments below).

In use, the conduit 104 would be installed into the patient through an opening in the bone 38 such that the distal end 108 is in the marrow space 40 and the proximal end 106 of the conduit 104 is outside of the patient, i.e., above their skin 36. The access port 102 may then be fixed to the patient's skin 36, i.e., by tape. When it is desired to sample bone marrow, the access port 102 is opened. Opening of the access port 102 may entail penetrating an elastomer diaphragm, valve and/or covering (not shown in this embodiment) using a needle or forceps for aspiration or biopsy. For example, a sampling device may be inserted through the internal channel in the housing of the access port 102 and then into the conduit 104 to the distal end 108 thereof and through one of the side holes 110 to contact and remove a marrow sample. The sampling device is then removed from the conduit 104 outside of the access port 102, and the access port 102 is then automatically or manually closed. This sampling procedure may be repeated. Also, a syringe may be attached to the port end that may allow direct aspiration.

The bone 38 may be the posterior iliac spine of the pelvis which is the traditional bone marrow access site, or it may access other less traditional sites such as the proximal femur or anterior iliac spine.

Figure 12:
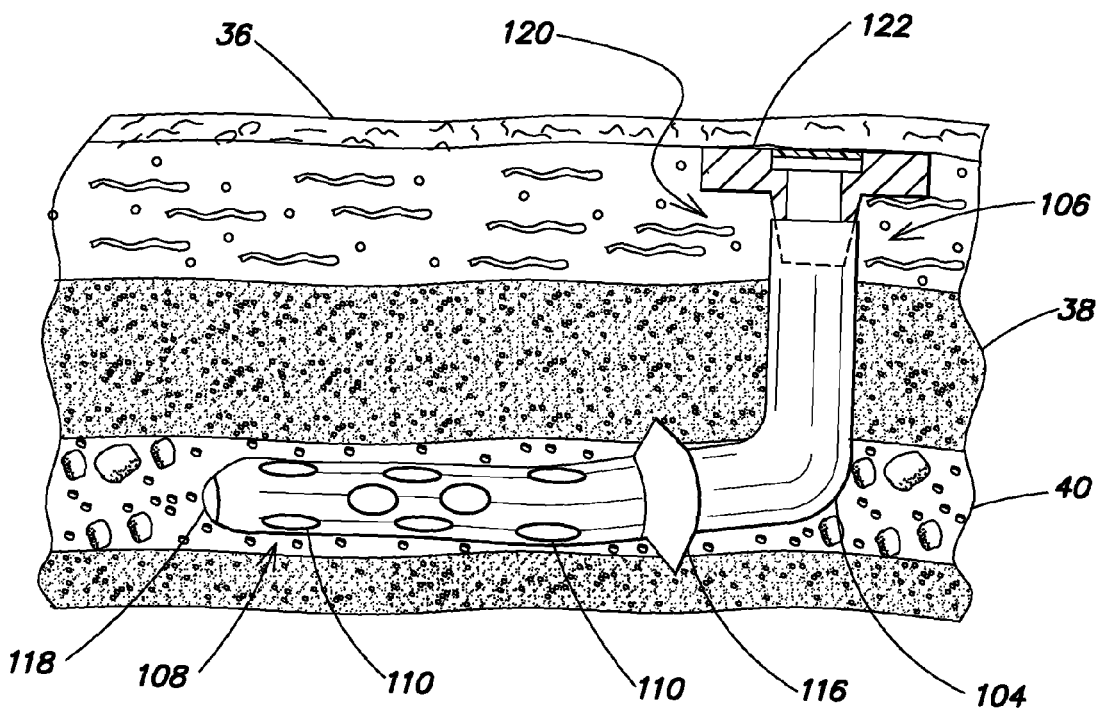
FIG. 12 shows yet another embodiment of bone marrow access apparatus in accordance with the invention.
Figure 14:
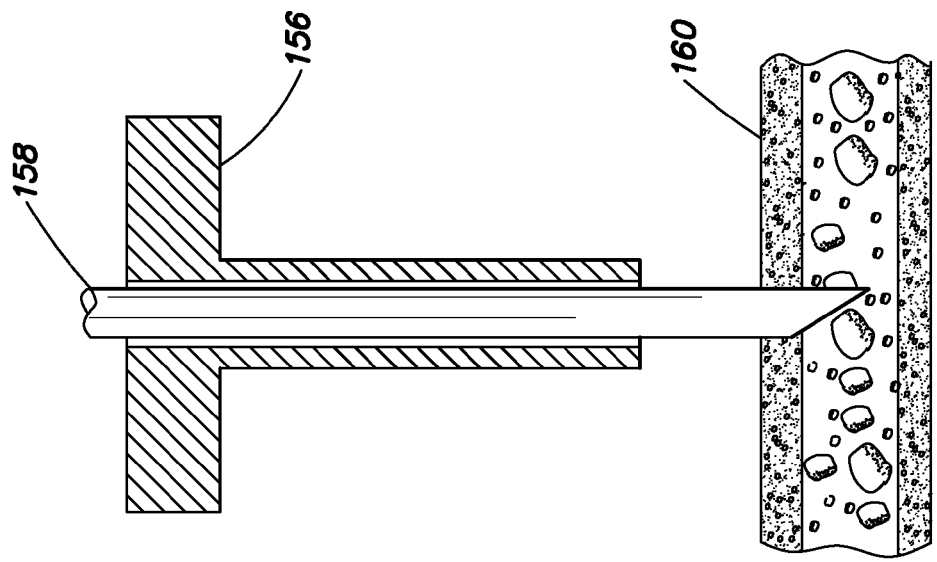
FIG. 14 shows the cannula of FIG. 13 in place with the needle removed and a biopsy/aspiration device passing through the cannula into a marrow space of a bone.
Figure 13:
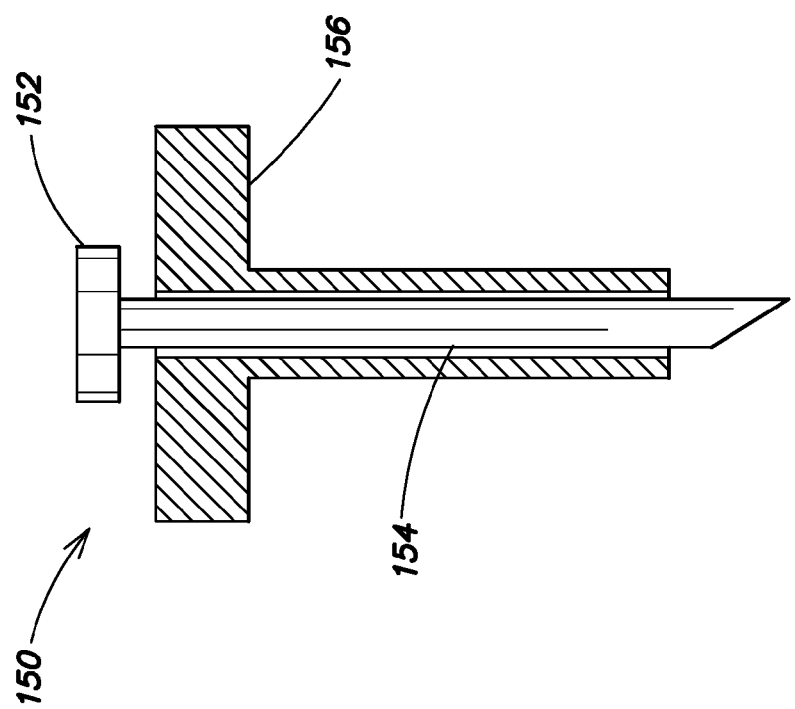
FIG. 13 shows a standard cannula and bone penetration needle.

FIG. 12 shows a second embodiment of a bone marrow access apparatus 120 in accordance with the invention with a subcutaneous access port 122 at one end of the conduit 104. Access port 122 includes a housing with an internal channel that communicates with the conduit 104. Access port 122 also includes an elastomer diaphragm, valve and/or covering over the internal channel (described in other embodiments below).

The installation and use of the bone marrow apparatus 120 is similar to the installation and use of the bone marrow apparatus 100 described above; however, the access port 122 is subcutaneous and therefore provisions must be taken to secure and maintain the access port 122 in a similar manner as subcutaneous access ports for other medical uses are secured and maintained. One skilled in the art of subcutaneous access ports, which are used, for example, for infusions, would understand the manner in which the access port 122 should be installed, maintained (cleaned) and accessed to allow for sterile access to the conduit 104 when bone marrow sampling is desired.

In the embodiments described above, the conduit 104 extends from the access port 102, 122, into the marrow space 40 of the bone 38. Conduit 104 may also be used with the embodiments of FIGS. 5-10, i.e., attached to the end of the access portions 52, 74, 90. In this case, the conduit 104 may have dimensions that correspond to the thickness of the cortex (bone 38) for the embodiment shown in FIGS. 5-10 wherein the access port 52, 74, 90 is on the bone 38, i.e., there is conduit outside of the bone 38, only in the marrow space 40. However, for the embodiments shown in FIGS. 11 and 12, the conduit 104 would extend several centimeters to the external location for the embodiment shown in FIG. 11, or extend several centimeters to the subcutaneous location for the embodiment shown in FIG. 12.

Any of the bone marrow access apparatus disclosed above enables repeated bone marrow access throughout a patient's therapy. Use of the bone marrow apparatus 10 is described above. For the bone marrow apparatus described in FIGS. 5-12, each access involves simply finding the access port, whether attached to the bone 38 (FIGS. 5-10), above the skin (FIG. 11), or beneath the skin (FIG. 12), and puncturing the diaphragm and/or valve associated with the access port. The diaphragm and/or valve may be designed to self-seal to enable repeated punctures, which feature is known to those skilled in the art of medical devices. A bone marrow biopsy needle can be used to take biopsy samples or a simple needle may be used for aspirations.

With respect to the embodiments shown in FIGS. 11 and 12, a bone marrow aspiration or biopsy method in accordance with the invention includes inserting a distal end 108 of the conduit 104 into the marrow space 40 in bone 38 through an opening of a bone penetration site of the bone 38. A proximal end 106 of the conduit 104 is coupled to the access port 102, 122 and includes a penetrable valve and/or an elastomer diaphragm. The distal end 108 of the conduit 104 is retained in the marrow space 40, e.g., by the internal retention device 116. The access port 102, 122 is retained at least partly exterior of the bone 38, e.g., exterior of the skin 36 (FIG. 11), or subcutaneously (FIG. 12). Then, at a plurality of spaced apart times while the distal end 108 of the conduit 104 is retained in the marrow space 40 and the access port 102, 122 is retained exterior of the bone 38, bone marrow is acquired by accessing the access port 102, 122 each time. The conduit 104 is not removed between the bone marrow acquisition procedures.

The aspiration or biopsy method for the bone marrow access apparatus including access ports 52, 74, 90 is slightly different when they do not include the conduit 104 and are attached directly to the bone 38.

For access port 74, the bone 38 is aligned at the bone penetration site 82, the opening 80 is formed at the bone penetration site 82, and the access port 74 is mounted to the bone 38 with the channels 70, 72 aligning at least partly with the opening 80 at the bone penetration site 82 by fixing it to the bone 38 using the securing members 88 (FIG. 9). For access port 90, the bone 38 is aligned at the bone penetration site 82, the opening 80 is formed at the bone penetration site 82 and the access port 90 is wedged into the opening 80 (FIG. 10).

Once therapy has been completed and the bone marrow access apparatus is no longer needed by the patient, the apparatus can be removed from the patient. For example, for the embodiment shown in FIGS. 5-10, removal may involve using a screw driver or comparable tool to unthread the access port from engagement with the bone 38.

In conjunction with the bone marrow access apparatus, additional accessories may be used to facilitate marrow acquisition. A kit in accordance with the invention would therefore include the bone marrow access apparatus in any of the disclosed embodiments and one or more of these accessories. Examples of accessories include forceps and core bone biopsy devices.

One exemplifying biopsy device might marry to the implanted device to enable proper alignment to reach the bone penetration site. Alignment may be facilitated by aligning a light emitted from the surface of the access port or having magnetic alignment from the bone marrow biopsy device on the outside lining up with the access port on the inside or having palpable connections.

Generally, an alignment mechanism may be incorporated into any of the access ports disclosed above. The alignment mechanism would enable personnel to properly align a biopsy needle with the bone penetration site. The alignment mechanism may be magnetic, physical, or illuminated. For example, the alignment mechanism may be constituted by the bumps 30, as an example of a palpable structure shown in FIGS. 3 and 4.

Similarly, various embodiments of the kit may include whatever tools and accessories are needed to accomplish implantation of a bone marrow access apparatus, tissue acquisition via the bone marrow access apparatus, and removal of the bone marrow access apparatus. For example, the trocar 44 shown in FIG. 4 may be used whenever guidance of a biopsy needle into an access port, conduit member, sheath or internal conduit is needed.

These tools may be used in a method for installing any of the embodiments of the bone marrow access apparatus described above. In a basic embodiment of the method, an opening into the marrow space 40 of the bone 38 is formed at a bone penetration site and the distal end 108 of the conduit 104 is inserted into the marrow space 40 through the formed opening at the bone penetration site. The distal end 108 is retained in the narrow space 40. The proximal end 106 of the conduit 104 that is coupled to the access port 102, 122 is retained at least partly exterior of the bone, e.g., exterior of the skin 36 (FIG. 11), or subcutaneously (FIG. 12). Other installation methods may also be used to install the bone marrow access apparatus described above.

The installation method for the bone marrow access apparatus including access ports 74, 90 will be different since they do not require the conduit 104 and may be attached directly to the bone. For example, a surgeon can directly install the access ports 74, 90 to the bone 38, fixing it to the bone 38 using the securing members 88 (FIG. 9) or wedging the access port 90 into the opening 80 in the bone 38 (FIG. 10).

Variations of the embodiments described above and illustrated in the drawings are considered to be within the scope of the invention, and thus the scope of the invention should be determined by the appended claims and their legal equivalents, rather than by the examples given.

The invention claimed is:

1. A bone marrow access apparatus, comprising:
a bone attachment part adapted to be attached to a bone, said bone attachment part including a flange and a housing having a hollow interior on a first side of said flange;
a tubular conduit part attached to said bone attachment part and defining a conduit communicating with said interior of said housing of said bone attachment part, said tubular conduit part extending away from said flange on a second side of said flange opposite said first side of said flange, and said tubular conduit part being made of a biocompatible material that is cuttable to a variable length;

a port which is attachable to said cut conduit part and spaced apart from said bone attachment part by said tubular conduit part, said port including a housing defining a hollow interior communicating with said conduit defined by said conduit part, wherein said hollow interior of said housing of said bone attachment part, said conduit of said conduit part and said hollow interior of said housing of said port define a passage;

a valve coupled to said housing of said port, wherein the valve has a conical shape with an open apex configured to be penetrated by a biopsy needle; and a flow control valve arranged at a distal end of said housing of said bone attachment part;

wherein said port comprises a localization part on or integrated into said port and configured to enable said port to be located through skin that covers said port.

2. The apparatus of claim 1, wherein said localization part comprises palpable structure on a surface of said housing of said port.

3. The apparatus of claim 1, wherein said conduit part is flexible.

4. The apparatus of claim 1, wherein said valve is arranged at a proximal end of said housing of said port.

5. The apparatus of claim 1, wherein said conduit part is permanently fixed to said bone attachment part.

6. The apparatus of claim 1, wherein said port includes an attachment structure to enable said port to be attached to said conduit part.

7. A bone marrow apparatus installation method utilizing the bone marrow access apparatus of claim 1, comprising:
    making an incision in a patient; then
    attaching the bone attachment part to a bone in the patient; and then
    closing the incision with the localization part in a position under skin of the patient.

8. The method of claim 7, further comprising changing a height or a length of the conduit part from an initial height to a length dependent on a distance between the bone attachment part and the patient's skin.

9. The method of claim 7, further comprising changing a height or a length of the port from an initial height to a length dependent on a distance between the bone attachment part and the patient's skin.

10. The method of claim 7, wherein the step of attaching the bone attachment part to the bone comprises fixing the bone attachment part into the bone.

11. A method for performing a bone marrow biopsy utilizing a bone marrow access apparatus, wherein said bone marrow access apparatus comprises:
    a bone attachment part adapted to be attached to a bone, said bone attachment part including a flange and a housing having a hollow interior on a first side of said flange;
    a tubular conduit part attached to said bone attachment part and defining a conduit communicating with said interior of said housing of said bone attachment part, said tubular conduit part extending away from said flange on a second side of said flange opposite said first side of said flange, and said tubular conduit part being made of a biocompatible material that is cuttable to a variable length;
    a port which is attachable to said cut conduit part and spaced apart from said bone attachment part by said tubular conduit part, said port including a housing defining a hollow interior communicating with said conduit defined by said conduit part, wherein said hollow interior of said housing of said bone attachment part, said conduit of said conduit part and said hollow interior of said housing of said port define a passage; and
    a valve coupled to said housing of said port, wherein the valve has a conical shape with an open apex configured to be penetrated by a biopsy needle;
    wherein said port comprises a localization part on or integrated into said port and configured to enable said port to be located through skin that covers said port;
said method comprising:
    in an installation stage,
        attaching the bone attachment part to a bone of a patient; and then
        covering the port with skin of the patient with the localization part in a position under the skin of the patient; and
    in a specimen sampling stage,
        inserting the biopsy needle through the skin above the port, through the valve and through the hollow interior of the housing of the port, into the conduit defined by the conduit part, and through the hollow interior of the housing of the bone attachment part into a marrow space;
        capturing marrow or tissue from the marrow space using the biopsy needle; and
        then removing the biopsy needle from the marrow space through the port, the conduit part and the bone attachment part.

12. The method of claim 11, further comprising, in the sampling stage before inserting the biopsy needle, inserting a trocar through the skin above the port, and through the hollow interior of the housing of the port until the trocar engages with the port, the trocar defining a guide for the insertion of the biopsy needle.

13. The method of claim 11, further comprising, in the specimen sampling stage before inserting the biopsy needle, locating the localization part to locate said port.

* * * * *